United States Patent
Frid

(10) Patent No.: US 8,728,031 B2
(45) Date of Patent: May 20, 2014

(54) COMPOUND FOR LOCAL DELETION OF TUMORS

(76) Inventor: Noureddine Frid, Beersel (BE)

( * ) Notice: Subject to any disclaimer, the term of this patent is extended or adjusted under 35 U.S.C. 154(b) by 375 days.

(21) Appl. No.: 13/120,817

(22) PCT Filed: Sep. 24, 2009

(86) PCT No.: PCT/EP2009/062385
§ 371 (c)(1),
(2), (4) Date: Jun. 3, 2011

(87) PCT Pub. No.: WO2010/034774
PCT Pub. Date: Apr. 1, 2010

(65) Prior Publication Data
US 2011/0224608 A1    Sep. 15, 2011

(30) Foreign Application Priority Data

Sep. 25, 2008 (EP) .................... 08165070

(51) Int. Cl.
*A61F 7/12* (2006.01)
(52) U.S. Cl.
USPC ........................................ 604/113
(58) Field of Classification Search
USPC ................. 604/113, 114, 65–67, 131, 151
See application file for complete search history.

(56) References Cited

U.S. PATENT DOCUMENTS 5,108,372 A *  4/1992  Swenson ............... 604/113
7,530,964 B2 *  5/2009  Lavi et al. ............. 604/110

FOREIGN PATENT DOCUMENTS

EP    1764085 A    3/2007

OTHER PUBLICATIONS

Ishibashi, T. et al., "Comparison of the Mode of Immuno Potentiating Action of BCG and Wax D Part 2 Effect on the Methyl Cholanthrene Carcinogenesis", Japanese Journal of Experimental Medicine, Jan. 1, 1977, pp. 435-440, vol. 47, No. 6, Institute of Medical Science, Tokyo, JP, XP009110653.*
WO 2007/083006.*
International Application No. PCT/EP2009/062385—PCT International Search Report mailed Oct. 26, 2009.
International Application No. PCT/EP2009/062385—PCT Written Opinion of the International Searching Authority mailed Mar. 25, 2011.
International Application No. PCT/EP2009/062385—PCT International Preliminary Report of Patentability completed Jan. 10, 2011.
Anonymous, "Wax", Internet Article, URL:http://en.wikipedia.org/wiki.Wax, Jan. 16, 2009, XP002510619.
Drissi, A. et al., "Tocopherols and saponins derived from *Argania spinosa* exert, an antiproliferative effect on human prostate cancer", Cancer Investigation, Sep. 1, 2006, pp. 588-592, vol. 24, No. 6, Marcel Dekker Inc., US, XP009110661.
Pettigrew, R. T. et al., "Clinical effects of whole-body hyperthermia in advanced malignancy", British Medical Journal, pp. 679-682, vol. 4, No. 5946, London, GB, XP009110667.

* cited by examiner

*Primary Examiner* — Manuel Mendez
(74) *Attorney, Agent, or Firm* — Miles & Stockbridge P.C.

(57) ABSTRACT

A compound for injecting locally into an intratumoral space of a body made of a mixture of a biocompatible wax, admixed with biocompatible oil. The compound is liquid at a temperature above body temperature but compatible with the life of healthy cells. It exhibits an increasing viscosity with decreasing temperature and becomes a solid close to body temperature. The compound is then metabolized by the human body.

13 Claims, 3 Drawing Sheets

COMPOUND FOR LOCAL DELETION OF TUMORS

CROSS REFERENCE TO RELATED APPLICATIONS

This application claims the benefit of PCT Application No. PCT/EP2009/062385, filed Sep. 24, 2009, now pending, which claims the benefit of and priority to European Application No. 08165070.7, filed Sep. 25, 2008, all of which are incorporated herein by reference in entirety.

FIELD OF THE INVENTION

The invention relates to a reversible liquefiable bio-compatible compound for inhibiting the growth of tumours like cancer tumours and to a delivery device for such a compound.

DESCRIPTION OF PRIOR ART

The main treatment methods for cancer, a disease that affects about 30% of the world's population, are today surgery and radiotherapy, particularly for solid tumours.

Both radiotherapy and surgery depend on the possibility to reach the affected areas and on the ability to treat the infected tissues. Surgery may be difficult or impossible to apply near to important or delicate structures.

Irradiation can be caused with X-ray or other heating ways as radio frequency, or ultrasounds. With radiotherapy the surgeons must frequently face the dilemma between destroying completely the tumour and causing serious damages to the surrounding healthy tissues. It is well known that the response of the cells to irradiation varies with the stage of the mitotic cycle. For example, in the DNA synthetic phase the cells are relatively resistant to X-rays. This may be due to the cell cycle effects. After its division, a cell undergoes a defined cycle of events, up to the time of its next division.

The non uniform heating caused by this method requires a constant repetition of the irradiation sessions.

Chemotherapy is also an important way of treatment and has led to significant improvements for certain types of neoplasm's, but its efficiency is still not proved, as a radical treatment, in the case of hard solid tumours.

Failures are often related to the difficulty to ensure that the drugs reach all the tumour cells.

Much attention is also focused on the study of the effect on some types of cancers of various dietary substances and in particular of their antioxidant properties, such as tea, olive oil, garlic, red wine, or argan oil (cf. e.g., Drissi et al (Cancer investigation, 21, 588-592, (2006)). Although some curative effect of an adequate diet on certain cancers cannot be discarded, consuming foodstuff having antioxidant properties is considered more as a preventive measure rather than a curative one.

Hyperthermia is another method of treatment. Broad and large, its general concept is based on the lower resistance of the cancerous cells to a rise of their internal temperature. Hyperthermia thus consists of selectively heating the tissues around cancerous cells.

This hyperthermia technique can be used with ferromagnetic particles. Phagocytizable particles capable of being inductively heated in response to an imposed high frequency alternating electromagnetic field are introduced in a part of the body for a local treatment. The time of treatment is correlated with the maximum responsiveness of particles in the tissues. This inductive heating of the particles is applied to obtain an increase in intracellular temperature, so as to selectively kill the cancerous cells.

The disadvantage of this method is that the particles may travel inside the body and embolize small vessels, as the pulmonary vessels. It can further lead to the development of renal insufficiency and to hypertonia crisis.

Pettigrew et al (British Medical J., 4, 679-682, (1974)) disclose an alternative hyperthermia technique consisting of covering a narcotized patient with molten wax at 50° C. to prevent evaporation of sweat and insulate the body. The overall effect is to raise the body temparture by 3 to 6° C. an hour depending on body weight. Such treatment may last up to 8 hours, with a constant control of the body water content and of the body temperature to not rise above 41.8° C. This method is very heavy for the patient timewise and in that the temperature of the whole body is raised. In this respect, much caution must be taken to protect the head from excess heat.

Another method is called Capsules drug delivery. It consists of administering liposomes, which are microscopic capsules of lipid or wax that contain potent doses of drugs like doxorubicin. It is known that the heating of the tumour opens up the pores in the vessels; accordingly, the liposome particles pass easily into the tumour.

This treatment shows limitations because the liposomes give up their content partially and slowly. Even if the release is fast it should be done at the adequate temperature.

Ishibashi et al. (Japan J. Exp. Med., 47, (6), 435-440, (1977) disclose the treatment of tumoral tissues by injection of a wax. An injection of small quantities of such wax, e.g., in the hind foot pad of mice, was reported to increase antibody formation.

According to another approach, one relies on an exothermic reaction provoked by the polymerisation of an injected substance (hard polymerized polymer as PMMA). This method has the drawback that a hardened polymerised substance is difficult to remove from the body.

The use of an exothermic polymerized polymer, like PMMA, can generate heat in excess, causing the temperature to raise up to between 50 and 120° C., which may result in a thermal necrosis of the surrounding healthy tissue.

The rheology of an exothermic polymer further does not allow an uniform distribution in the tumour.

Another approach which raises great hopes is the asphyxia of tumours. Such asphyxia can be caused for example by preventing the development of blood vessels feeding the tumours.

SUMMARY OF THE INVENTION

The object of the invention is the development of a compound able to be injected locally into the body of a patient, able to carry heat at a desired temperature in such a way that when in contact with the tumour cells, it will be able to destroy or to de-activate them.

Another object of the invention is that said compound can be resorbed by the body.

Another object of the invention is to prevent blood from reaching the tumour.

Another object of the invention is to develop a delivery system which allows controlled injection of said compound.

The subject of the invention is defined in the appended independent claims. Preferred embodiments are defined in the dependent claims. In particular, the present invention concerns a wax compound for the treatment of internal tumoral tissues. A wax compound in the present context means that it comprises a wax as a main component in its composition. "Hawley's Condensed Chemical Dictionary," 13th Ed., (John Wiley & Sons) 1997, p. 1178, defines a "wax" as a "low melting organic mixture or compound of high molecular weight, solid at room temperature and generally similar in composition to fats and oils except that it contains no glycerides."

The wax compound of the present invention preferably comprises a biocompatible wax miscible in a biocompatible oil, said compound being liquid at a temperature above body temperature but compatible with the life of healthy cells, exhibiting an increasing viscosity with decreasing temperature and becoming a solid close to body temperature, this solidification process being reversible by application of heat.

The advantages of such a compound are that it can be injected by direct needle puncture access into intratumoral spaces of a body. This compound can be heated up to a temperature compatible with the life of healthy cells but lethal for tumour cells. Further, as it exhibits an increasing viscosity with decreasing temperature, a sealing effect can be obtained, avoiding leakage into draining veins.

The wax is preferably candellila wax.

The compound preferably comprises Argan oil, which according to the tests carried out is miscible with candelilla wax and allows an easy control of the compound's viscosity at the desired temperature ranges.

According to an advantageous embodiment said compound is liquid above 40° C., preferably in the range of 40-45° C., and most preferably in the range of 41-43° C., which ranges correspond to preferred temperature windows of injection.

According to a preferred embodiment it comprises a contrast liquid miscible with the wax and the oil, and is visible with current radiological imaging methods including X-ray and nuclear magnetic resonance techniques.

According to an advantageous embodiment, it is metabolizable by a human body.

The ratio wax/oil is preferably chosen so that the viscosity of the compound is in the range of 3 to 30 mPa·s at a temperature close to body temperature at injection conditions in terms of temperature and flow rate.

Another subject of the invention is a delivery device for a compound as defined above comprising a storage tank containing a wax compound as defined above heated by a heating device, a temperature regulating thermostat, a pump for circulating the wax compound, valving means for deviating a part of the circulating wax compound towards an injection needle device.

BRIEF DESCRIPTION OF THE DRAWINGS

Other aspects and advantages of the invention will become apparent from the description hereinafter of various embodiments, reference being made to the drawings, wherein.

The figures are not drawn to scale. Generally, identical components are denoted by the same reference numerals in the figures.

DETAILED DESCRIPTION OF THE INVENTION

Figure 1:
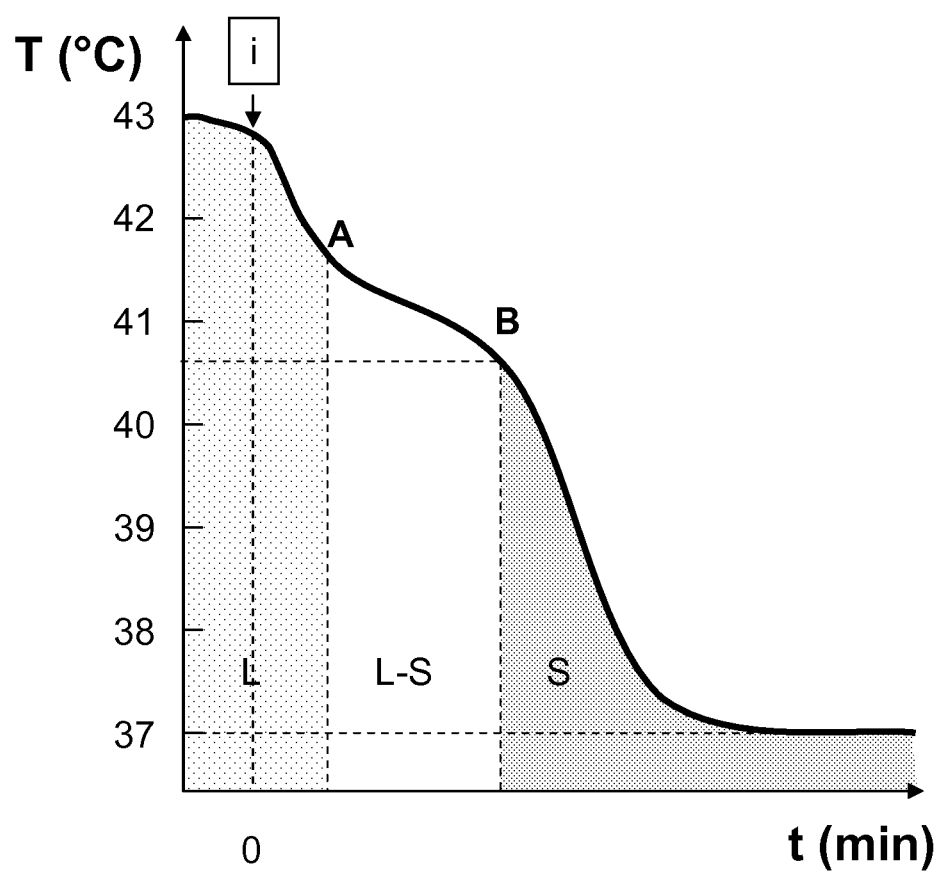
FIG. 1 is a graph representing the variation of temperature versus time upon cooling of a theoretical wax compound representative of the present invention.

The compound and devices of the invention were developed for heating tumour's cells up to a temperature around 41° C. by incorporating a heated bio-compatible substance, which will be described below. We found out that an important factor was the presence or absence of molecular oxygen in the tumoral cells. In other words the oxygen seems to be a most important metabolite when using heating effects: with less oxygen the tumour's sensitivity to the temperature is increased.

Since vasculation is fundamental in the cell oxygenation process, it must be taken into account in the hyperthermia treatment.

As explained below, healthy human cells continue to thrive under high temperatures around 45° C. and beyond. In contrast, the growth of many tumorous cells decreases, attesting of their destruction, in a range of 41-43° C.

From a biochemical point of view, the effects of the method using the present compound are:
 the local rise of the temperature of the affected cells;
 the suppression of oxygen supply to the tumoral cells;
 the suppression of nutrients as glucose for growth and division; the oxidation of glucose can no more be accomplished;
 the disequilibrium of the pH by an acidity increase,
 the suppression of cellular proteins synthesis.

Factors Affecting the Tumour Destruction by Heat:

It is important to mention that tumours frequently grow in the form of cylinders of cells that obtain their supplies of oxygen and other nutrients from the surrounding vasculature. Capillaries do not penetrate into these 'rods' of cells, maybe because they grow faster than the formation of capillaries. Earlier on, in 1955, authors like Thomlinson and Gray (The histological structure of some human lung cancers and possible implications for radiotherapy, Brit J Cancer 9,539, 1955) showed that bands of healthy tissues are about 150 μm thick; it seems the maximum thickness that can be reached by tissues for them to be oxygenated and to remain adequately supplied in nutrients from outside. Beyond this limit a necrosis phenomenon appears.

A low pH and a deficiency in nutrients are other important factors which also play a role in the sensitivity of the cells to heat. The hypoxic cells have a tendency towards anaerobic metabolism (thus producing lactic acid). It is most likely that after injection of the wax, there will be regions of the tumours with a pH lower than the physiological pH, which will render them more heat sensitive.

The treatment uses current image guided minimally invasive techniques to identify tumour location and volume. Under such visual control, the tumour mass is accessed under sterile conditions using direct needle puncture techniques.

Identification of intratumoral location is obtained by injection of a contrast material, allowing for analysis of the intratumoral spaces that are accessible by the needle puncture.

Treatment planning is used to define the amount of time required to subsequently heat the compound to obtain a heating effect on the adjacent tumour tissue surrounding the solid implant.

To fulfil the requirements defined above, the compound should preferably display the following properties:
 A viscosity between 3 and 30 mPa·s, which allows it to be carried out with available filling devices such as needles or special catheters;
 It better should melt just before the injection at a very precise regulated temperature;
 It should be able to flow and to surround a tumour (the flow, mainly along the surface where the tumour is active, is an important factor) to isolate it from its environment in such a way that no oxygen and no nutrients can reach it any more;

Finally, it must be bio-compatible, being in intimate contact with body organs. The term bio-compatible is defined in Webster's dictionary as being "compatible with living tissue, as a prosthetic material or device that is not rejected or does not cause infection".

FIG. 1 displays the time-temperature cooling curve of a wax according to the present invention after injection in a body (cf. injection point in time "i"=0). The shoulder between points A and B corresponds to the solidification stage (L-S) of the wax compound, whilst it is a liquid (L) before point A, and it is a solid (S) after point B. The start (point A) and duration (time between A and B) of said solidification stage are of great importance for the successful treatment by injection of the wax compound. The optimal wax rheology will depend on several factors such as the size of the region to be treated, the amount of wax, the injection speed, the position in the body of the tumour, the ease of access with a needle to said position, etc.

Figure 2:
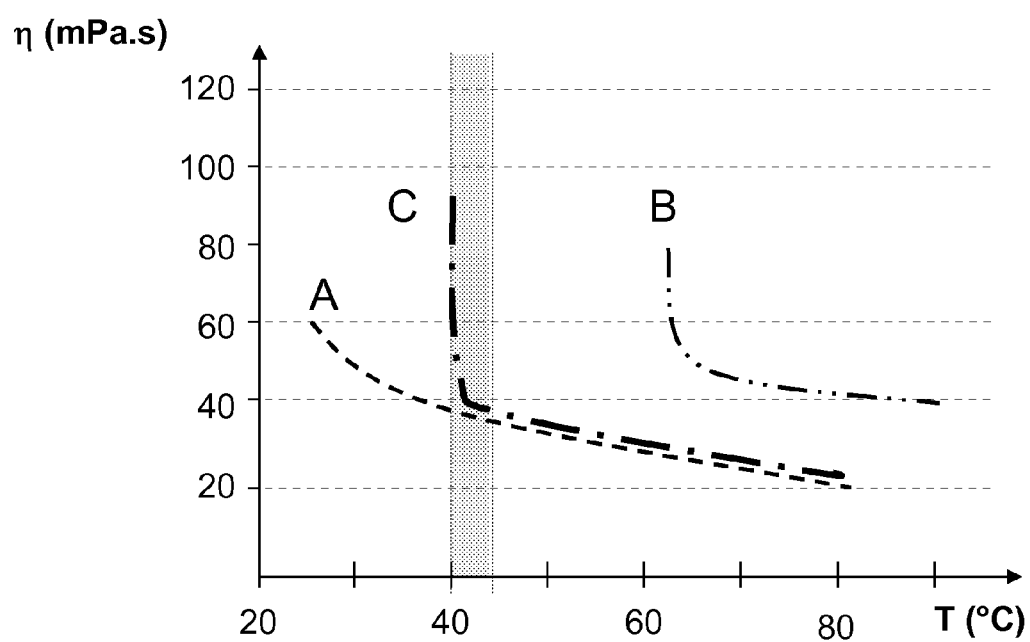
FIG. 2 is a graph representing the variation of viscosity of different components used in the compound of the invention.

FIG. 2 is a graph representing the viscosity-temperature curve of two main components of the compound of the invention, namely a wax (curve B) and an oil (curve A) to dilute said wax, either alone or mixed in given proportions (curve C). The shaded area represents the temperature window for injection of the wax compound. Injection should preferably be executed at temperatures of 40° C. or more, since the wax compound should be a solid or at least be sufficiently viscous to be set at body temperatures below 40° C., and should not exceed temperatures of 45° C., lest neighbouring healthy cells could be burnt. A preferred injection temperature is comprised between 40 and 44° C., more preferably, between 41-43° C., most preferably around 42° C.

One wax which meets all the requirements listed above is natural Candelilla wax which is considered as a bio-compatible substance by the Food and Drug Administration. This wax is produced from small shrubs from Mexico (Euphorbiaceae). It consists primarily of hydrocarbons with odd-numbered straight carbon chains from C29 to C33 together with esters of acids with even-numbered carbon chains from C28 to C34; free acids, free alcohols, sterols neutral resins and mineral matter are also present. It is classed as hard wax and has a fuse temperature ranging from 64 to 71° C.

This wax is often used in the cosmetic and pharmaceutical industries. In patent GB 1066277, candelilla wax is saponified and used as an emulsifying agent in dandruff shampoo formulations. In U.S. Pat. No. 6,403,619, candelilla wax is used as a carrier for a pro-DNA agent to control cell necrosis or apoptosis.

Candelilla wax can also be used in food stuffs like candies or dough to improve stability and texture. In DE-4121901, candelilla wax enters into the composition of coatings for baked goods prepared from dough, rendering them impermeable to moisture and suitable for human consumption.

Though candelilla wax appears as the most adequate substance to fulfil the requirement set forth for the described method, it is obvious that other suitable waxes can also be used.

One of the major requirements for the compound is its ability to reversibly solidify, i.e., to be able to be re-melted later if necessary. The second requirement is that the substance would neither polymerise nor crosslink during the tumour filling phase as it may happen with some polymers (this is a key point which differentiates the use of the invention from the use of hard polymerized polymers as PMMA).

Candelilla wax would allow a good control and monitoring of the temperature level. However, when used alone, it proves too solid and its viscosity is too high, so that it is difficult to inject and further, it blocks up injection devices as the temperature decreases.

Other problems arose when tests were carried out to find a thinner suitable for this particular wax. "Classical" biocompatible thinners proved unsuccessful, the mixture rapidly separating into two distinct phases. A particular oil, Argan oil, however, allowed to obtain the required properties. In the graph shown at FIG. 2, e.g., curve C is obtained with a compound comprising 5.54% argan oil.

Argan oil is a particular oil extracted from Argan tree (Argania Spinosa). This tree is to be found exclusively in South-West Morocco. Owing to the restricted area in which it grows, Argan tree represents a priceless patrimonial treasure for Morocco.

Argan oil is extracted traditionally from a paste manufactured from the crushed "almonds" of pear-form fruits of the Argania Spinosa.

In traditional medicines, argan oil is used in dermatology for its regenerating properties, to cure the hairs and the nails. It begins to be used in beauty care and, as mentioned supra, its antioxidant properties when ingested are being more and more recognized (cf. Drissi et al. (op. cit.)).

Argan oil is non-saponifiable (which contribute to its recognized high quality), soluble merely in chloroform or hexane, slightly soluble in ethanol, non-miscible with water.

The local treatment method described above is safer and more effective than irradiation with X-ray or other heating ways as radio frequency, or ultrasounds.

For example, the cells in the DNA synthetic phase are, on the one hand relatively resistant to X-ray and, on the other hand particularly sensitive to heat. This may be due to the cell cycle effects, as stated above.

One can combine radiation and heat to get more effective results because there is a dual mechanism of interaction between hyperthermia and irradiation: to increase the biological effect of a given radiation dose (hyperthermic radiosensitisation) and to destroy radio-resistant tumour cells (hyperthermic cyto-toxicity).

Figure 3:
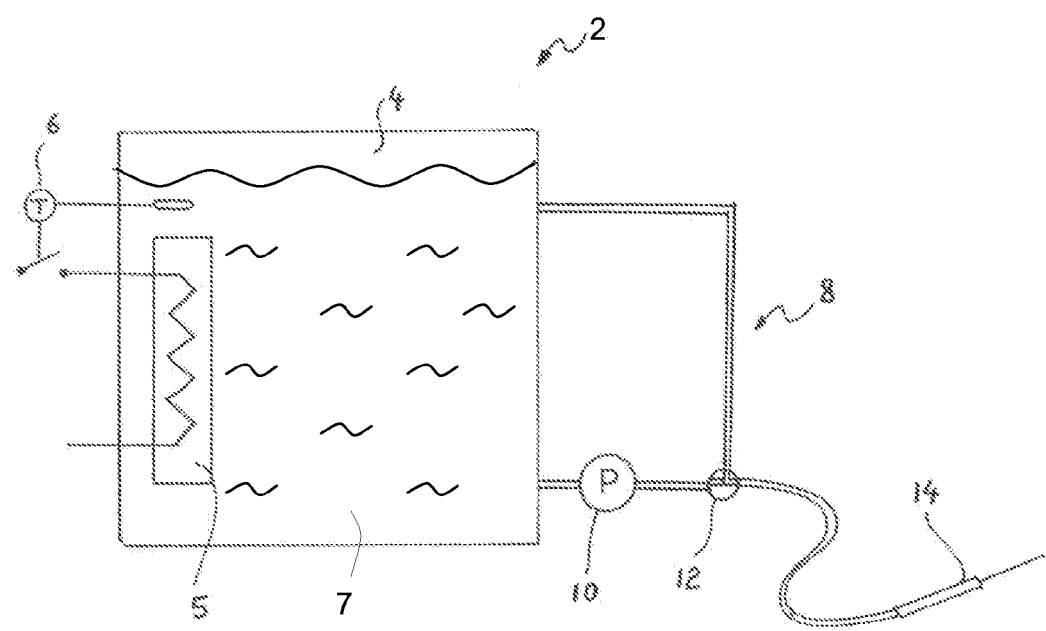
FIG. 3 is a sketch of a delivery device used for the injection of the compound.

FIG. 3 shows a device (2) for injecting the wax compound (7) of the present invention. This device (2) comprises a compound storage tank (4) containing a wax compound (7) heated by a heating device (5), a temperature regulating thermostat (6), a by-pass (8) for the liquefied compound with a pump (10) for circulating the compound outside the tank (2), valving means (12) for deviating a part of the circulating implant material towards an injection needle device (14).

The heated compound is injected in its liquid form through the injection needle (14) to reach the intratumoral spaces and to fill progressively such preformed spaces, including vascular and necrotic cavities.

It is to be noted that the needle used to inject the compound is normally larger in diameter than a classical injection needle.

The injection of the liquid compound is performed at a speed that allows a control of its delivery, avoiding leakages into the venous drainage of the tumoral vascular spaces. Generally, a plurality of injections is required to enclose the whole tumour. The compound, being in the liquid phase, flows along the surface of the tumour and solidifies in about 2 minutes. However, as soon as it meets another volume of compound (injected through another puncture), it liquefies again and mixes with said new volume, allowing the whole tumour to be eventually surrounded by a film of solidified compound. Of course, it is up to the surgeon to choose carefully the injection sites, density and angles.

Visualization of the solid compound volume is performed, and if deemed necessary, additional amounts are added so as to ensure a complete encirclement of the tumour.

Imaging methods are used to assess the result and the heating can be performed on desire to repeat the anti-tumoral heating effect obtained by secondary stimulation of the solid wax compound.

In order to improve the visibility of the implant, an opaque compound can be added to the wax compound.

Once the hyperthermic treatment is deemed to have produced its effect, it is not necessary to withdraw the compound from the patient's body. Both the candellila wax and the Argan oil can be metabolized by the body, so that they trickle away, leaving no traces whatsoever.

Nevertheless, if large quantities of compound have been used, it is possible to remove at least partially this compound by re-heating it and sucking it out through a device as described for injection.

The presence of an opaque compound mixed to the waxy material allows to monitor the amount of wax material remaining in the patient's body and to stop the recovery operation as soon as no more trace of the opaque compound is detected.

One may think that the effect of the wax would be limited, the heat treatment affecting merely the peripheral tumoral cells. It seems nevertheless that this does not affect the deletion process of the tumour at all, the "active" cancerous cells being precisely the peripheral ones.

The invention claimed is:

1. A wax compound for use in local treatment of internal tumoral tissues by injection thereof into an intratumoral space, said wax compound comprising as main components a biocompatible wax in admixture with a biocompatible oil, said compound being liquid at a temperature above body temperature which is compatible with the life of healthy cells, said compound exhibits an increasing viscosity with decreasing temperature and becomes a solid close to body temperature, this solidification process being reversible by application of heat, the ratio wax/oil being chosen so that the viscosity of the compound is in the range of 3 to 30 mPa·s at injection conditions in terms of temperature and flow rate.

2. The wax compound according to claim 1 wherein it comprises candellila wax.

3. The wax compound according to claim 1 wherein it comprises Argan oil.

4. The wax compound according to claim 1 wherein the transition between solid and liquid state of said compound occurs in the range of 40-45° C.

5. The wax compound according to claim 4 wherein the transition between solid and liquid state of said compound occurs in the range of 41-43° C.

6. The wax compound according to claim 1 wherein it further comprises a contrast liquid miscible with the wax and/or, if any, the oil, and is visible with current radiological imaging methods including X-ray and nuclear magnetic resonance techniques.

7. The wax compound according to claim 1 wherein it is metabolizable by a human body.

8. The wax compound according to claim 1 wherein it comprises a mixture of candellila wax and Argan oil.

9. The wax compound according to claim 8 wherein the transition between solid and liquid state of said compound occurs in the range of 40-45° C.

10. The wax compound according to claim 9 wherein the transition between solid and liquid state of said compound occurs in the range of 41-43° C.

11. The wax compound according to claim 8 wherein it is metabolizable by a human body.

12. A method of local treatment of internal tumoral tissues with an injectable wax compound, the method comprising following steps of:

providing a wax compound storage tank containing the wax compound, said wax compound being metabolizable by a human body and comprising as main components candellila wax in admixture with Argan oil so said compound being liquid at a temperature above body temperature which is compatible with the life of healthy cells, said wax compound exhibiting an increasing viscosity with decreasing temperature and becoming a solid in the range of 40-45° C., close to body temperature, this solidification process being reversible by application of heat, the ratio wax/oil being chosen so that the viscosity of the compound is in the range of 3 to 30 mPa·s at injection conditions in terms of temperature and flow rate, heating the wax compound with heating means connected to a thermostat to heat the wax compound to an injection temperature, said heating means being provided with said tank, a pump for circulating the wax compound at its injection temperature, and valving means constructed to deviate a part of the circulating wax compound towards an injection needle device, and injecting the heated wax compound into an intratumoral space.

13. A wax compound for use in local treatment of internal tumoral tissues by injection thereof into an intratumoral space, said wax compound, metabolizable by a human body, comprising as main components candellila wax in admixture with Argan oil wherein said compound being liquid at a temperature above body temperature which is compatible with the life of healthy cells and exhibiting an increasing viscosity with decreasing temperature and becoming a solid in the range of 40-45° C., close to body temperature, this solidification process being reversible by application of heat, the ratio wax/oil being chosen so that the viscosity of the compound is in the range of 3 to 30 mPa·s at injection conditions in terms of temperature and flow rate.

* * * * *